United States Patent [19]

Surber et al.

[11] Patent Number: 4,931,566
[45] Date of Patent: Jun. 5, 1990

[54] PROCESS FOR THE PREPARATION OF PYRROLO[3,4-C]PYRROLES

[75] Inventors: Werner Surber, Oberwil; Abul Iqbal, Arconciel; Christian Stern, Kaiseraugst, all of Switzerland

[73] Assignee: Ciba-Geigy Corporation, Ardsley, N.Y.

[21] Appl. No.: 218,770

[22] Filed: Jul. 14, 1988

[30] Foreign Application Priority Data

Jul. 31, 1987 [CH] Switzerland .................. 2935/87

[51] Int. Cl.$^5$ .................................. C07D 471/02
[52] U.S. Cl. .................... 548/453; 546/167; 546/144; 546/268; 548/159; 548/217; 548/336; 548/454; 548/455
[58] Field of Search .............. 548/453, 159, 217, 336, 548/454, 455; 546/144, 167, 268

[56] References Cited

U.S. PATENT DOCUMENTS

| | | | |
|---|---|---|---|
| 4,415,685 | 11/1983 | Iqbal et al. | 524/92 |
| 4,490,542 | 12/1984 | Iqbal et al. | 548/453 |
| 4,579,949 | 4/1986 | Rochat et al. | 548/453 |
| 4,585,878 | 4/1986 | Jost et al. | 548/453 |
| 4,613,669 | 9/1986 | Cassar et al. | 546/167 |
| 4,659,775 | 4/1987 | Pfenninger et al. | 524/92 |
| 4,720,305 | 1/1988 | Iqbal et al. | 107/494 |
| 4,778,899 | 10/1988 | Pfenninger et al. | 548/453 |

FOREIGN PATENT DOCUMENTS 3525109  1/1987  Fed. Rep. of Germany ...... 548/453

Primary Examiner—David B. Springer
Attorney, Agent, or Firm—Stephen V. O'Brien

[57] ABSTRACT

Process for the preparation of 1,4-diketopyrrolo[3,4-c]pyrroles of the formula I

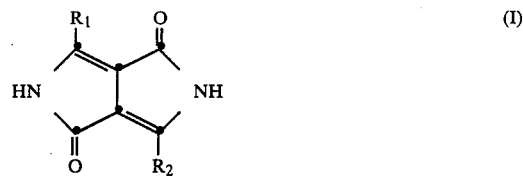

in which $R_1$ and $R_2$ independently of one another are phenyl, biphenyl or naphthyl radicals or aromatic O-heterocyclic, S-heterocyclic or N-heterocyclic radicals, by reacting 1 mole of a dicyclohexyl succinate, dialkyl succinate, monoalkylmonophenyl or diphenyl succinate, alkyl in the succinic acid ester radical being $C_1$–$C_{18}$alkyl and phenyl being phenyl which is unsubstituted or substituted by one or two halogen atoms or one or two $C_1$–$C_6$alkyl or $C_1$–$C_6$alkoxy groups, with 2 moles of a nitrile of the formula II or III or with 1 mole of a nitrile of the formula II and 1 mole of a nitrile of the formula III $$R_1\text{—CN}, \quad (II)$$

$$R_2\text{—CN} \quad (III)$$

in which $R_1$ and $R_2$ are as defined above, in an inert organic solvent, in the presence of an alkali metal or an alkali metal alcoholate, as a strong base, and at an elevated temperature to give an alkali metal salt of the formula IV

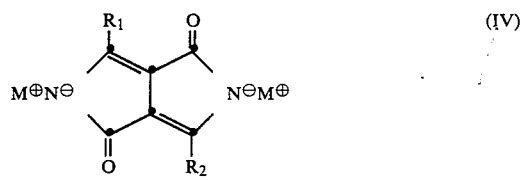

in which M is an alkali metal, and subsequently liberating a compound of the formula I by protolysis of a compound of the above formula IV, which comprises treating, in stages, a compound of the above formula IV in at least two portions, as a protolysing agent, with water, with an inorganic and/or organic acid, with a mixture of water and an organic solvent, or with a mixture of an inorganic or organic acid and water and/or at least one organic solvent, and reacting the mixture at a temperature from 20° to 150° C. after the addition of each of the portions.

15 Claims, No Drawings

PROCESS FOR THE PREPARATION OF PYRROLO[3,4-C]PYRROLES

The invention relates to an improved process for the preparation of 1,4-diketopyrrolo[3,4-c]pyrroles, which are valuable pigments.

EP Patent No. 94,911 describes a process for the preparation of 1,4-diketopyrrolo[3,4-c]pyrroles, in which 1 mole of a succinic acid diester is reacted with 2 moles of a single-substance nitrile or a mixture of two different nitriles in an organic solvent, in the presence of a strong base and at an elevated temperature, and the pyrrolopyrrole is liberated from the resulting reaction product by hydrolysis. In the hydrolysis or protolysis stage, the protolysis agent is added all at once to the reaction products formed in the first stage of the process (alkali metal salts or alkaline earth metal salts of the diketopyrrolopyrroles), water, an alcohol or an acid being used for this purpose. The products obtained by this process can, in general, be employed as pigments without further treatment in the form in which they are obtained after their synthesis, although their chemical purity is not always optimal and their pigment properties often do not fully satisfy the requirements of industry. A subsequent chemical or heat after-treatment of the products obtained by this process is therefore often required. For example, for conversion into a hiding pigment form, these products must in most cases be subjected to an after-treatment by heat in an organic solvent, which requires an additional, separate process stage and, in addition, quite often results in the formation of undesirable by-products.

It has now been found that pyrrolopyrrole pigments of high purity and excellent pigment properties can be obtained directly if the protolysis of the reaction products obtained in accordance with the above EP Patent is carried out in stages. In this case the formation of undesirable by-products and degradation products can be suppressed greatly with a simultaneous improvement in the coloristic properties, such as saturation, clarity of colour shade and gloss, add also the properties in use of the pigments, such as rheology, gloss and fastness to light and weathering.

Accordingly, the invention relates to a process for the preparation of 1,4-diketopyrrolo[3,4-c]pyrroles of the formula I

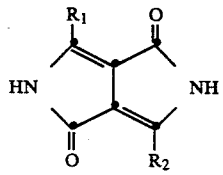

(I)

in which $R_1$ and $R_2$ independently of one another are phenyl, biphenyl or naphthyl radicals or aromatic O-heterocyclic, S-heterocyclic or N-heterocyclic radicals, by reacting 1 mole of a dicyclohexyl succinate, dialkyl succinate, monoalkylmonophenyl or diphenyl succinate, alkyl in the succinic acid ester radical being $C_1$–$C_{18}$alkyl and phenyl being phenyl which is unsubstituted or substituted by one or two halogen atoms or one or two $C_1$–$C_6$alkyl or $C_1$–$C_6$alkoxy groups, with 2 moles of a nitrile of the formula II or III or with 1 mole of a nitrile of the formula II and 1 mole of a nitrile of the formula III $$R_1\text{—CN,} \qquad (II)$$

$$R_2\text{—CN} \qquad (III)$$

in which $R_1$ and $R_2$ are as defined above, in an inert organic solvent, in the presence of an alkali metal or an alkali metal alcoholate, as a strong base, and at an elevated temperature to give an alkali metal salt of the formula IV

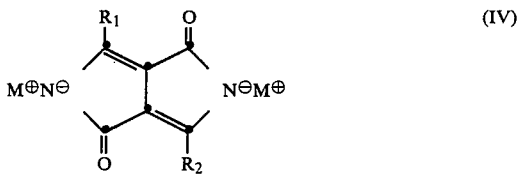

(IV)

in which M is an alkali metal, and subsequently liberating a compound of the formula I by protolysis of a compound of the above formula IV, which comprises treating, in stages, a compound of the above formula IV in at least two portions, as a protolysing agent, with water, with an inorganic and/or organic acid, with a mixture of water and an organic solvent, or with a mixture of an inorganic or organic acid and water and/or at least one organic solvent, and reacting the mixture at a temperature from 20° to 150° C. after the addition of each of the portions.

If $R_1$ and $R_2$ are phenyl, biphenyl or naphthyl radicals, they can contain the customary substituents which impart insolubility in water, for example:

(1) halogen atoms, for example chlorine, bromine or fluorine;

(2) branched or unbranched alkyl groups having preferably 1 to 8, in particular 1 to 4, C atoms. Examples of alkyl groups are methyl, ethyl, n-propyl, isopropyl, n-butyl, sec-butyl, tert-butyl, n-pentyl, tert-amyl, n-hexyl, 1,1,3,3-tetramethylbutyl, n-heptyl and n-octyl;

(3) the groups —CN, —CF$_3$, —NO$_2$, —COOH, —CONH$_2$ or —SO$_3$H;

(4) alkoxy groups containing 1 to 3 C atoms, phenoxy or phenoxy which is substituted by one or two halogen atoms or one or two alkyl or alkoxy groups having 1 to 3 C atoms. Examples of these are methoxy, ethoxy, n-propoxy, phenoxy, o-, m- or p-chlorophenoxy, o-, m- or p-methylphenoxy, p-ethoxyphenoxy or p-bromophenoxy;

(5) the group alkylmercapto having 1 to 3 C atoms and phenylmercapto which can be substituted by one or two halogen atoms or one or two alkyl or alkoxy groups having 1 to 3 C atoms. Examples of alkylmercapto are methylmercapto, ethylmercapto and n-propylmercapto; examples of phenylmercapto are phenylmercapto, p-chlorophenylmercapto and p-methylphenylmercapto;

(6) the group dimethylamino or diethylamino;

(7) the group alkoxycarbonyl containing 2 to 5 C atoms. Examples of this are methoxycarbonyl, ethoxycarbonyl, n-propoxycarbonyl and n-butoxycarbonyl;

(8) the group $C_2$–$C_5$alkanoylamino, for example acetylamino, propionylamino or butyrylamino, and also benzoylamino which can be substituted by one or two halogen atoms or one or two alkyl or alkoxy groups having 1 to 3 C atoms, for example benzoylamino, p-chlorobenzoylamino and p-methylbenzoylamino.

If $R_1$ and $R_2$ are radicals of aromatic O-heterocyclic, S-heterocyclic or N-heterocyclic compounds, they can be unsubstituted or substituted by, for example, halogen, such as chlorine, bromine or fluorine, or alkyl or alkoxy containing 1 to 3 C atoms. Examples of heterocyclic radicals of this type are quinolyl, isoquinolyl, o-, m- or p-pyridyl, furanyl, thiofuranyl, benzoxazolyl, benzthiazolyl and benzimidazolyl radicals.

Preferred N-heterocyclic radicals are o-, m- and p-pyridyl.

The compounds of the formula I are prepared in accordance with the invention by using, as the starting material, preferably a single-substance nitrile of the formula II or III in which $R_1$ and $R_2$ are phenyl or naphthyl radicals.

It is preferable to use as the starting materials nitriles of the formula V

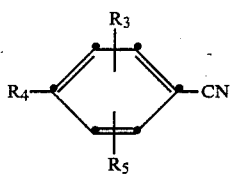
(V)

in which $R_3$, $R_4$ and $R_5$ independently of one another are hydrogen, fluorine, chlorine, bromine, carbamoyl, cyano, trifluoromethyl, $C_1$–$C_8$alkyl, $C_1$–$C_3$alkylmercapto, $C_2$–$C_5$alkoxycarbonyl, $C_2$–$C_5$-alkanoylamino, N-dimethylamino, N-diethylamino; or are phenoxy, phenylmercapto or benzoylamino, each of which is unsubstituted or substituted by one or two halogen atoms or one or two $C_1$–$C_3$alkyl or $C_1$–$C_3$alkoxy groups, at least one of the substituents $R_3$, $R_4$ and $R_5$ being hydrogen.

It is very particularly preferable to use as starting materials nitriles of the formula VI

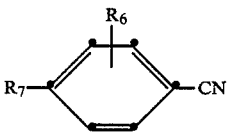
(VI)

in which $R_6$ and $R_7$ independently of one another are hydrogen, chlorine, bromine, fluorine, methyl, methoxy, ethoxy, cyano; or are phenoxy or phenylmercapto, each of which is unsubstituted or substituted by chlorine or methyl; or are methoxycarbonyl, ethoxycarbonyl, acetylamino or benzoylamino which is unsubstituted or substituted by chlorine, methyl or methoxy.

Starting materials which are very particularly used are nitriles of the above formula VI in which one of the substituents $R_6$ and $R_7$ is as defined above and the other is hydrogen.

The dialkyl or diphenyl succinates to be used can be symmetrical or asymmetrical diesters. It is preferable, however, to use symmetrical diesters of succinic acid, in particular symmetrical dialkyl succinates. If a diphenyl or monophenylmonoalkyl succinate is present, phenyl can be, for example, phenyl which is unsubstituted or substituted by one or two halogen atoms, such as chlorine, $C_1$–$C_6$alkyl groups, such as methyl, ethyl, isopropyl or tert-butyl, or $C_1$–$C_6$alkoxy groups, such as methoxy or ethoxy. Phenyl is preferably unsubstituted phenyl. If a dialkyl or mono-alkylmonophenyl succinate is concerned, alkyl can be unbranched or branched, preferably branched, and can preferably contain 1 to 12 C atoms, in particular 1 to 8 C atoms and particularly preferably 1 to 5 C atoms. Branched alkyl is preferably sec-alkyl or tert-alkyl, for example iso-propyl, sec-butyl, tert-butyl and tert-amyl. It is very preferable to use symmetrical, branched dialkyl succinates in which each alkyl radical in the succinic acid ester radical has 3 to 5 C atoms.

Examples of succinic acid diesters are dimethyl, diethyl, dipropyl, dibutyl, dipentyl, dihexyl, diheptyl, dioctyl, diisopropyl, di-sec-butyl, di-tert-butyl, di-tert-amyl, di-[1,1-dimethylbutyl], di-[1,1,3,3-tetramethylbutyl], di-[1,1-dimethylpentyl], di-[1-methyl-1-ethylbutyl], di-[1,1-diethylpropyl], diphenyl, di-[4-methylphenyl], di-[2-methylphenyl], di-[4-chlorophenyl], di-[2,4-dichlorophenyl] and monoethyl monophenyl succinate.

The succinic acid diesters listed above and the nitriles of the formula II or III are known compounds and can be prepared by known processes.

The reaction of the succinic acid diester with the nitrile of the formulae II or III or a mixture thereof is carried out in an inert organic solvent. Examples of suitable solvents are primary, secondary or tertiary alcohols having 1 to 10 C atoms, such as methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol and 2,4,4-trimethyl-2-pentanol, glycols, such as ethylene glycol or diethylene glycol, and also ethers, such as tetrahydrofuran or dioxane, or glycol ethers, such as ethylene glycol monomethyl or dimethyl ether, ethylene glycol monoethyl or diethyl ether, diethylene glycol monomethyl ether or diethylene glycol monoethyl ether, and also dipolar aprotic solvents, such as acetonitrile, benzonitrile, dimethylformamide, N,N-dimethylacetamide, nitrobenzene and N-methylpyrrolidone, aliphatic or aromatic hydrocarbons, such as benzene or benzene which is substituted by alkyl, alkoxy or halogen, such as toluene, xylenes, anisole or chlorobenzene, or aromatic N-heterocyclic compounds, such as pyridine, picoline or quinoline. Additionally, it is also possible to use an excess of the nitrile of the formula II or III to be reacted at the same time as the solvent, if it is liquid in the temperature range in which the reaction takes place. The solvents mentioned above can also be employed in the form of mixtures. It is advantageous to use 5–20 parts by weight of solvent for 1 part by weight of the reactants.

The solvent preferably used in the process according to the invention is an alcohol, especially a secondary or tertiary alcohol. Preferred tertiary alcohols are tert-butanol and tert-amyl alcohol. In this regard mixtures of these or mixtures of these preferred solvents with aromatic hydrocarbons, such as toluene or xylenes or benzenes which are substituted by halogen, such as chlorobenzene or o-dichlorobenzene, are also of great interest.

Strong bases which are suitable in accordance with the application are alkali metals, such as lithium, sodium and potassium, and alkali metal alcoholates derived, in particular, from primary, secondary or tertiary aliphatic alcohols having 1 to 10 C atoms, for example lithium methylate, ethylate, n-propylate, isopropylate, n-butylate, sec-butylate, tert-butylate, 2-methyl-2-butylate, 2-methyl-2-pentylate, 3-methyl-3-pentylate and 3-ethyl-3-pentylate, sodium methylate, ethylate, n-propylate, isopropylate, n-butylate, sec-butylate, tert-butylate, 2-methyl-2-butylate, 2methyl-2-pentylate, 3-methyl-3- pentylate and 3-ethyl-3-pentylate or potassium methylate, ethylate, n-propylate, isopropylate, n-butylate, sec-butylate, tert-butylate, 2-methyl-2-butylate, 2-methyl-2-pentylate, 3-methyl-3-pentylate and 3-ethyl-3-pentylate. It is also possible, however, to use a mixture of the alkali metal alcoholates mentioned above. It is preferable to use alkali metal alcoholates in which alkali is, in particular, sodium or potassium and in which the alcoholate is preferably derived from a secondary or tertiary alcohol. Strong bases which are particularly preferred are therefore, for example, sodium isopropylate, sec-butylate, tert-butylate and tert-amylate or potassium isopropylate, sec-butylate, tert-butylate and tert-amylate. Moreover, it is also possible to prepare the alkali metal alcoholates in situ by reacting the corresponding alcohol with the alkali metal.

The strong base can be employed in the process according to the invention in an amount of, for example, 0.1 to 10 mol, preferably 1.9 to 4.0 mol, relative to 1 mol of the succinic acid diester. Although in principle stoichiometric amounts of the base are sufficient, in many cases an excess of base has a favourable effect on the yield.

The reaction can be carried out, for example, at a temperature from 60° to 140° C., but a temperature from 80° to 120° C. is preferable.

The succinic acid diester can, in principle, be reacted with the nitrile or nitriles of the formulae II, III, V and VI by initially taking all the components at a fairly low temperature and then warming up the mixture into the range of the reaction temperature, or to add the individual components in any desired sequence within the range of the reaction temperature. A preferred embodiment which, as a rule, has a particularly advantageous effect on the yield consists in initially taking the nitrile to be reacted together with the strong base and metering in the succinic acid diester within the range of the reaction temperature. A further possible method is to meter the succinic acid diester and the nitrile to be reacted simultaneously into the base initially taken. It is entirely possible to carry out the process according to the invention not only batchwise, but also continuously.

Particularly in the case of succinic acid diesters containing lower alkyl radicals and in the case of alcoholates derived from lower alcohols, for example methanol, ethanol, n-propanol, isopropanol or tert-butanol, it can prove advantageous to remove the lower alcohol formed in the reaction continuously from the reaction medium in order to achieve higher yields.

If the solvent used is an alcohol and the base used is an alcoholate, it can be advantageous to select an alcohol and an alcoholate having identical alkyl moieties. It can also be advantageous if, in addition, the succinic acid diester also contains just such alkyl groups.

The protolysing agents which are suitable in accordance with the invention can be used in any desired mixing ratios for protolysing the resulting condensation products of the formula IV. It is advantageous to use 5 to 20 parts by weight of the protolysing agent to 1 part of a compound of the formula IV.

Examples of organic acids as protolysing agents are aliphatic or aromatic carboxylic or sulfonic acids, for example formic acid, acetic acid, propionic acid, butyric acid, hexanoic acid, oxalic acid, benzoic acid, phenylacetic acid, benzenesulfonic acid or p-toluenesulfonic acid.

Examples of suitable inorganic acids are hydrochloric acid, sulfuric acid or phosphoric acid.

Examples of mixtures of an inorganic acid and an organic acid are mixtures of the acids mentioned above.

Organic solvents which are suitable for use in accordance with the invention as protolysing agents are, in principle, the same solvents which have already been mentioned above for the first process stage (condensation stage). Alcohols having 1 to 5 C atoms, such as methanol, ethanol, propanol, isopropanol, tert-butyl alcohol and tert-amyl alcohol, are preferred.

Protolysing agents which are preferred in accordance with the invention are water, mixtures of water and an aliphatic alcohol, in particular methanol, ethanol or tert-amyl alcohol, and also water mixed with an acid, in particular acetic acid, HCl or $H_2SO_4$, or a mixture of water, an acid and an organic solvent, for example water, hydrochloric acid or acetic acid and methanol or ethanol or tert-amyl alcohol or toluene or xylene. It is very particularly preferred to use water on its own or mixtures of water and methanol in any desired ratios.

For protolysing the reaction product of the formula IV it is possible, in principle, initially to take, at a low temperature, the alkali metal salt of the formula IV formed in the first process stage and then to add at least 2 portions of the protolysing agent within the range of the reaction temperature, or, preferably, initially to take the protolysing agent and then to add the product of the formula IV in at least two portions. The size of the portions can be varied as desired. Portion sizes between 5 and 75 per cent by weight, preferably 10 to 50 per cent by weight, of the total amount, relative to the product of the formula IV or to the protolysing agent, have proved advantageous, stirring being continued for one to several hours, if appropriate under pressure, after the addition of each portion.

The reaction temperature in the protolysis stage is preferably between 50° and 100° C. Depending on the size of the batch, the reaction time can be, for example, 1 to 12 hours, preferably 1 to 8 hours.

If the protolysis stage is carried out without water, the amount of acid is advantageously 1 to 4 equivalents, preferably 1 to 2 equivalents, relative to the amount of alkali metal salt of the formula IV.

It is preferable in accordance with the invention to carry out the protolysis stage in 2 portions, the first portion of the protolysing agent or of the compound of the formula IV being 40 to 50% by weight of the total amount.

The compounds of the formula I are precipitated after the protolysis and can be isolated by methods of separation which are known per se, such as filtration Depending on the nature of their substituents and on the polymers to be coloured, the compounds of the formula I can also be used as polymer-soluble dyes. As a rule, however, they are used as pigments for high-molecular organic materials. In this case the pigments are in most cases employed directly in the pigment form in which they are obtained by the process according to the invention. Their crystal morphology can be optimized further, depending on the end use and the necessity for this, by means of a subsequent treatment. Thus the pigment can first be isolated, for example after the protolysis stage, and subsequently heated in water or in an organic solvent, if appropriate under pressure, in order, for example, to obtain an opaque or more opaque form. It is preferable to use organic solvents boiling above 80° C. Solvents which have proved particularly suitable are benzenes substituted by halogen atoms or alkyl or nitro groups, such as xylenes, chlorobenzene, o-dichlorobenzene or nitrobenzene, and pyridine bases, such as pyridine, picoline or quinoline, and also ketones, such as cyclohexanone, ethers, such as ethylene glycol monomethyl or monoethyl ether, amides, such as dimethylformamide or N-methylpyrrolidone, and dimethyl sulfoxide or sulfolane. The after-treatment can also be carried out in water in the presence of organic solvents and/or with added surface-active substances.

Depending on the end use, it can be advantageous to prepare mixtures of compounds of the formula I. This can be carried out, for example, by mixing, before protolysis, different reaction solutions which have been prepared independently of one another, protolysing them together and then isolating the resulting product.

Examples of high-molecular organic materials which can be dyed or pigmented by means of the compounds of the formula I are cellulose ethers and esters, such as ethylcellulose, nitrocellulose, cellulose acetate and cellulose butyrate, natural resins and synthetic resins, such as polymerization resins or condensation resins, for example aminoplasts, in particular urea/formaldehyde and melamine/formaldehyde resins, alkyd resins, phenoplasts, polycarbonates, polyolefins, such as polyethylene and polypropylene, polystyrene, polyvinyl chloride, polyacrylonitrile, polyacrylic acid esters, polyamides, polyurethanes, polyesters, rubber, casein, silicone and silicone resins, individually or as mixtures.

It is unimportant in this regard whether the high-molecular organic compounds mentioned are in the form of plastic compositions, melts or spinning solutions, coatings, paints or printing inks. Depending on the end use, it proves advantageous to employ the compounds of the formula I as toners or in the form of preparations. Relative to the high-molecular organic material to be pigmented, the compounds of the formula I can be employed in an amount of 0.01 to 30% by weight, preferably 0.1 to 10% by weight.

The colorations obtained, for example in plastics, fibres, lacquers or prints, are distinguished by good dispersibility, great depth of colour, good fastness to overlacquering, migration, heat, light and weathering and by good gloss.

In the following examples parts are parts by weight.

EXAMPLE 1

357.9 g of 4-chlorobenzonitrile are added under an atmosphere of nitrogen to a solution of alcoholate prepared from 90.1 g of sodium and 1,560 ml of tert-amyl alcohol, and the resulting mixture is heated to 85° C. 262.6 g of diisopropyl succinate are then added dropwise in the course of 80 minutes at 85°–95° C., and the resulting suspension is stirred for a further two hours at this temperature. Half of the pyrrolopyrrole sodium salt suspension (226.5 g) formed is discharged into 700 ml of water and stirred under reflux for 8 hours. The remaining 50 per cent (=226.5 g) of the above sodium salt suspension are then added at 85° C., and the suspension obtained is stirred under reflux for one hour.

The tert-amyl alcohol is then removed completely from the reaction mixture by subjecting the latter to steam distillation. The aqueous suspension remaining is filtered while hot, and the filter cake is washed until neutral with 6 liters of hot water and dried under vacuum in an oven at 120° C. A red pigment of the following formula

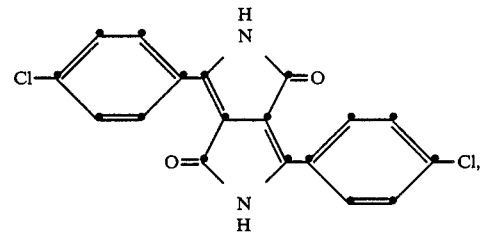

which has excellent coloristic and pigment properties, is obtained in this way.

EXAMPLES 2 to 17

A procedure analogous to that of Example 1 is employed, under those conditions described in Table 1 below for the stagewise protolysis, using ditert-butyl succinate instead of diisopropyl succinate. In each case products having excellent pigment properties are obtained, and the formation of undesirable by-products and degradation products can be considerably suppressed.

TABLE 1

| | Stagewise protolysis of the sodium salt suspension | | | | |
|---|---|---|---|---|---|
| | first portion | | second portion | | |
| Example No. | Amount, % by weight, of the Na salt suspension | Subsequent stirring, duration (hours) | Amount, % by weight, of the Na salt suspension | Subsequent stirring, duration (hours) | Protolysing agent |
| 2 | 50 | 7 | 50 | 1 | Water |
| 3 | 50 | 4 | 50 | 1 | Water |
| 4 | 50 | 4 | 50 | 8 | Water |
| 5 | 50 | 8 | 50 | 1 | Water |
| 6 | added in 8 portions of equal weight over 8 hours | | | | Water |
| 7 | 50 | 1 | 50 | 5 | Water |
| 8 | 50 | 1 | 50 | 8 | Water |
| 9 | 25 | 8 | 75 | 1 | Water |
| 10 | 25 | 4 | 75 | 5 | Water |
| 11 | 75 | 4 | 25 | 4 | Water |
| 12 | 50 | 8 | 50 | 1[(1)] | Water |
| | | | | | Methanol:Water[(2)] |
| 13 | 50 | 4 | 50 | 8 | 1:4 |
| 14 | 50 | 2 | 50 | 2 | 1:1 |
| 15 | 50 | 4 | 50 | 8 | 4:1 |
| 16 | 50 | 6 | 50 | 3 | Methanol/glacial acetic acid[(3)] (50% of stoichiometric amount) |
| 17 | 50 | 4 | 50 | 4 | tert-Amyl alcohol/glacial |

TABLE 1-continued

| | Stagewise protolysis of the sodium salt suspension | | | | |
|---|---|---|---|---|---|
| | first portion | | second portion | | |
| Example No. | Amount, % by weight, of the Na salt suspension | Subsequent stirring, duration (hours) | Amount, % by weight, of the Na salt suspension | Subsequent stirring, duration (hours) | Protolysing agent |
| | | | | | acetic acid (50% of stoichiometric amount) |

[1]the conditioning temperature after the 2nd half of the sodium salt suspension has been added is 50° C. instead of 85–90° C. (reflux temperature);
[2]Ratio by volume;
[3]% of stoichiometric amount = % of the amount of glacial acetic acid required by stoichiometry for complete neutralization.

EXAMPLES 18–22

A procedure analogous to that of Example 1 is employed, under the conditions described in Table 2 below for the protolysis stage, using ditert-butyl succinate instead of diisopropyl succinate. In each case products having excellent pigment properties are obtained.

the conditions of protolysis described in Table 3, a product of the formula

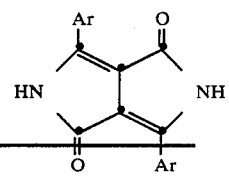

TABLE 2

| | Stagewise protolysis of the sodium salt suspension* | | | | | |
|---|---|---|---|---|---|---|
| | first portion | | second portion | | Protolysing agent | |
| Example No. | Amount, % by weight, of the Na salt suspension | Subsequent stirring, duration (hours) | Amount, % by weight, of the Na salt suspension | Subsequent stirring duration (hours) | Constituents | Ratio by volume |
| 18 | 50 | 2 | 50 | 2 | Water/methanol and glacial acetic acid (50% of stoichiometric amount**) | 1:1 |
| 19 | 50 | 6 | 50 | 3 | Water + glacial acetic acid (100% of stoichiometric amount**) | |
| 20 | 50 | 4 | 50 | 8 | Glacial acetic acid/water | 4:1 |
| 21 | 50 | 4 | 50 | 8 | Dioxane/water | 4:1 |
| 22 | 50 | 4 | 50 | 8 | Ethanol/water | 4:1 |

*Conditioning temperature after protolysis of each Na salt suspension = reflux temperature of the particular reaction mixture present.
**% of stoichiometric amount = % of the amount of glacial acetic acid required by stoichiometry for complete neutralization.

EXAMPLES 23–28

A procedure analogous to that of Example 1 is employed, using ditert-butyl succinate instead of diisopropyl succinate and using a nitrile of the formula ArCN listed in Table 3 instead of p-chlorobenzonitrile. Under the conditions of protolysis described in Table 3, a product of the formula having excellent pigment properties is obtained in each case.

TABLE 3

| | | Stagewise protolysis of the sodium salt suspension* | | | | | |
|---|---|---|---|---|---|---|---|
| | | first portion | | second portion | | Protolysing agent | |
| Example No. | Nitrile (Ar—CN) | Amount, % by weight, of the Na salt suspension | Subsequent stirring, duration (hours) | Amount, % by weight, of the Na salt suspension | Subsequent stirring, duration (hours) | Constituents | Ratio by volume |
| 23 | phenyl—CN | 50 | 2 | 50 | 2 | (according to Example 1) | |
| 24 | pyridyl—CN | 50 | 2 | 50 | 2 | Methanol/water and glacial acetic acid (100% of stoichiometric amount**) | 4:1 |
| 25 | pyridyl—CN | 50 | 2 | 50 | 2 | Methanol/water and glacial acetic acid (100% of stoichiometric amount**) | 4:1 |

TABLE 3-continued

| Example No. | Nitrile (Ar—CN) | Stagewise protolysis of the sodium salt suspension* | | | | Protolysing agent | |
|---|---|---|---|---|---|---|---|
| | | first portion | | second portion | | | |
| | | Amount, % by weight, of the Na salt suspension | Subsequent stirring, duration (hours) | Amount, % by weight, of the Na salt suspension | Subsequent stirring, duration (hours) | Constituents | Ratio by volume |
| 26 | CH₃—C₆H₄—CN (para) | 50 | 2 | 50 | 2 | Methanol/water | 4:1 |
| 27 | CH₃—C₆H₄—CN (meta) | 50 | 2 | 50 | 2 | Methanol/water | 4:1 |
| 28 | biphenyl-CN | 50 | 4 | 50 | 4 | Methanol/water | 4:1 |

*Conditioning temperature of the protolysis suspension in a particular case:
Example 23 = 40° C.;
Examples 24–28 = reflux temperature of the particular reaction mixture present.
**% of stoichiometric amount = % of the amount of glacial acetic acid required by stoichiometry for complete neutralization.

Use Examples

EXAMPLE 29

(plasticized polyvinyl chloride)

0.6 g of the pigment of Example 1 above are mixed with 67 g of polyvinyl chloride, 33 g of dioctyl phthalate, 2 g of dibutyltin dilaurate and 2 g of titanium dioxide, and the resulting mixture is worked on a roll mill for 15 minutes at 160° C. to give a thin film. The red PVC film thus produced has a deep colour and is fast to migration and light.

EXAMPLE 30

(polyethylene)

0.2 part of the pigment of Example 1 above, 1 part of titanium dioxide (rutile) and 100 parts of LD polyethylene granules are mixed in a drum, and the mixture is then worked on mixing rolls at 130° C. The composition is compression-moulded or shaped in an extruder to give sheets. The sheets exhibit a beautiful red coloration of good fastness to light.

EXAMPLE 31

(alkyd/melamine stoving enamel)

60 parts of a 60% solution of a non-drying alkyd resin in xylene (tradename ®Beckosol 27-320, made by Reichhold-Albert-Chemie), 36 parts of a 50% solution of a melamine/formaldehyde resin in a butanol/xylene mixture (tradename ®Super-Beckamin 13-501 made by Reichhold-Albert-Chemie), 2 parts of xylene and 2 parts of glycol monomethyl ether are mixed, and 100 parts of this mixture are stirred by means of a stirrer to give a homogeneous coating solution.

95 parts of the clear coating thus obtained and 5 parts of the pigment of Example 1 above are dispersed for 72 hours in a ball mill. The coloured coating is then applied to sheet metal by a customary spraying method and is stoved for 30 minutes at 120° C. This gives a coat of good fastness to light.

What is claimed is:

1. In the process for the preparation of a 1,4-diketopyrrolo[3,4]-pyrrole of the formula I

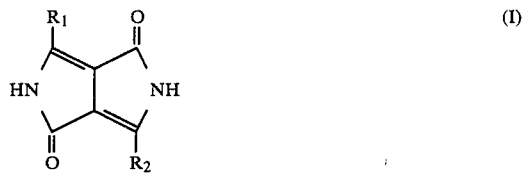

in which $R_1$ and $R_2$ independently of one another are phenyl, biphenyl or naphthyl radicals or aromatic heterocycles selected from the group consisting of quinolyl, isoquinolyl, o-, m-, p-pyridyl, furanyl, thiofuranyl, benzoxazolyl, benzthiazolyl, and benzimidazolyl radicals, by reacting 1 mole of a dicyclohexyl succinate, dialkyl succinate, monoalkylmonophenyl or diphenyl succinate, alkyl in the succinic acid ester radical being $C_1$–$C_{18}$alkyl and phenyl being phenyl which is unsubstituted or substituted by one or two halogen atoms or one or two $C_1$–$C_6$alkoxy groups, with 2 moles of a nitrile of the formula II or III or with 1 mole of a nitrile of the formula II and 1 mole of a nitrile of the formula III $R_1$—CN,      (II)

$R_2$—CN      (III)

in which $R_1$ and $R_2$ are as defined above, in an inert organic solvent, in the presence of an alkali metal or an alkali metal alcoholate, as a strong base, and at elevated temperature to give an alkali metal salt of the formula IV

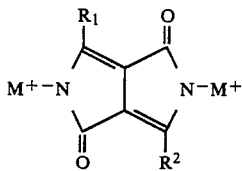

in which M is an alkali metal, and subsequently liberating a compound of the formula I by protolysis of a compound of the above IV, the improvement consisting of (a) dividing the compound of formula IV into at least two portions, adding each portion sequentially into a protolysis medium of water, an inorganic acid, an organic acid, a mixture of an inorganic and an organic acid, a mixture of water and an organic solvent, a mixture of an organic acid and water or a mixture of an inorganic acid or an organic acid with water and/or at least one organic solvent, or (b) dividing a protolysis medium of water, an inorganic acid, an organic acid, a mixture of an inorganic and an organic acid, a mixture of water and an organic solvent, a mixture of an organic acid and water or a mixture of an inorganic acid or an organic acid with water and/or at least one organic solvent into at least two portions, adding each portion sequentially to the compound of formula IV, and reacting the resulting mixture in each instance at a temperature from 20° to 150° C. after each addition.

2. A process according to claim 14, wherein the starting material used is a single-substance nitrile of the formula II or III in which $R_1$ and $R_2$ are phenyl or naphthyl radicals.

3. A process according to claim 14, wherein the starting materials used are nitriles of the formula II or III in which $R_1$ and $R_2$, as aromatic N-heterocyclic radicals, are o-, m- or p-pyridyl.

4. A process according to claim 14 wherein the starting materials used are nitriles of the formula V

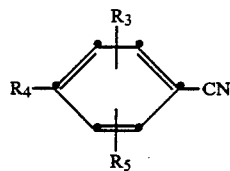

in which $R_3$, $R_4$ and $R_5$ independently of one another are hydrogen, fluorine, chlorine, bromine, carbamoyl, cyano, trifluoromethyl, $C_1$–$C_8$-alkyl, $C_1$–$C_3$alkoxy, $C_1$–$C_3$alkylmercapto, $C_2$–$C_5$-alkanoylamino, N-dimethylamino, N-diethylamino; or are phenoxy, phenylmercapto or benzoylamino, each of which is unsubstituted or substituted by one or two halogen atoms or one or two $C_1$–$C_3$alkyl or $C_1$–$C_3$alkoxy group, at least one of the substituents $R_3$, $R_4$ and $R_5$ being hydrogen.

5. A process according to claim 14, wherein the starting materials used are nitriles of the formula VI

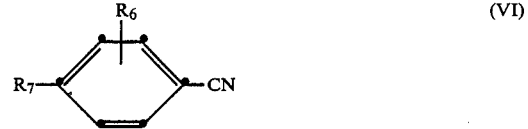

in which $R_6$ and $R_7$ independently of one another are hydrogen, chlorine, bromine, fluorine, methyl, methoxy, ethoxy, cyano; or are phenoxy or phenylmercapto, each of which is unsubstituted or substituted by chlorine or methyl; or are methoxycarbonyl, ethoxycarbonyl, acetylamino or benzoylamino which is unsubstituted or substituted by chlorine, methyl or methoxy.

6. A process according to claim 5, wherein one of the substituents $R_6$ and $R_7$ is as defined in claim 5 and the other is hydrogen.

7. A process according to claim 14, wherein the dialkyl succinate used is a symmetrical, branched dialkyl succinate in which each alkyl radical in the succinic acid ester radical has 3 to 5 C atoms.

8. A process according to claim 14, wherein the solvent used for the first reaction stage is a secondary or tertiary alcohol.

9. A process according to claim 14, wherein the strong base used is an alkali metal alcoholate.

10. A process according to claim 14, wherein the reaction in the first reaction stage is carried out at a temperature from 60° to 140° C.

11. A process according to claim 14, wherein the organic solvent used for the protolysis is an alcohol having 1 to 5 C atoms.

12. A process according to claim 14, wherein the protolysing agent used is water, mixtures of water and an aliphatic alcohol, water mixed with an acid, or a mixture of water, an acid and an organic solvent.

13. A process according to claim 12, wherein water on its own or water/methanol mixtures are used.

14. A process according to claim 1, wherein the protolysis stage is carried out in two portions, the first portion of the protolysing agent or of the compound of the formula IV being 40 to 50% by weight of the total amount.

15. A process according to claim 1, wherein the temperature in the protolysis stage is between 50° and 100° C.

* * * * *